United States Patent [19]
Chupakhin et al.

[11] Patent Number: 6,117,867
[45] Date of Patent: Sep. 12, 2000

[54] SUBSTITUTED 6-R-1,3,4-THIADIAZINE-2-AMINES, THE USE THEREOF AS ANAESTHETIZING, CARDIOVASCULAR AND HYPOMETABOLIC AGENTS, AND A PHARMACEUTICAL COMPOSITION CONTAINING THEM

[75] Inventors: Oleg Nikolaevich Chupakhin; Larisa Petrovna Sidorova; Emma Afanasievna Tarakhty; Antonina Petrovna Novikova; Natalya Mikhailovna Perova, all of Ekaterinburg; Valentin Antonovich Vinogradov, Moscow, all of Russian Federation; Michiel Franciscus van Ginkel, Amstelveen, Netherlands

[73] Assignees: Procter & Gamble Company, Cincinnati, Ohio; Nauchno-Tekhnologicheskoepredpriyatie "Ligand"(Tovarischestvo S Organichennol Otvetstvennostju), Ekaterinburg Ulitsa Mira, Russian Federation

[21] Appl. No.: 09/101,080
[22] PCT Filed: Dec. 28, 1995
[86] PCT No.: PCT/RU95/00285
  § 371 Date: Aug. 18, 1998
  § 102(e) Date: Aug. 18, 1998
[87] PCT Pub. No.: WO97/24354
  PCT Pub. Date: Jul. 10, 1997
[51] Int. Cl.[7] .................. A61K 31/549; C07D 417/12
[52] U.S. Cl. ............................ 514/222.5; 544/8
[58] Field of Search ................. 544/8; 514/222.5

[56] References Cited

U.S. PATENT DOCUMENTS

| | | | |
|---|---|---|---|
| 3,956,311 | 5/1976 | Kuffner et al. | 260/310 A |
| 4,272,532 | 6/1981 | Jones et al. | 424/246 |
| 4,309,426 | 1/1982 | Jones, Jr. et al. | 424/246 |
| 4,558,045 | 12/1985 | Hargreaves et al. | 514/222 |
| 4,645,528 | 2/1987 | Diehr et al. | 71/90 |
| 4,940,790 | 7/1990 | Thorwart et al. | 544/8 |
| 5,021,413 | 6/1991 | Terada et al. | 514/227.5 |
| 5,411,955 | 5/1995 | Strasser et al. | 514/214 |

FOREIGN PATENT DOCUMENTS

| | | |
|---|---|---|
| 884990 | 12/1980 | Belgium . |
| 884991 | 12/1980 | Belgium . |
| 2493844 | 5/1982 | France . |
| 3031703 | 3/1981 | Germany . |
| 3042295 | 6/1982 | Germany . |
| 220311 | 3/1985 | Germany . |
| 228248 | 10/1985 | Germany . |
| 288824 | 4/1991 | Germany . |
| 4988889 | 8/1974 | Japan . |
| 6253976 | 9/1994 | Japan . |
| 1726478 | 4/1992 | U.S.S.R. . |
| 1827257 | 7/1993 | U.S.S.R. . |
| 2215206 | 9/1989 | United Kingdom . |

OTHER PUBLICATIONS

Beyer,H. "Desulfurization Reactions with the Formation of Pyrazoles." Z. Chem.9 JG. (1969) p. 369 (with English Translation) with English Translation of DD 288824 Dated Apr. 1991.

Pfieffer, W.D. et al. "About Contraction of the Ring of 6H 1,3,4–Thiadiazines . . . " Synthesis, No. 7 (1977) pp. 485–486 (with English Translation).

"Evaluation of the Effect of Narcotic, Analgetic and Psychotropic Agents in Clinical Anesthesiology." N. A. Psipova, The Meditsina Publishers, Leningrad, Chapter 2 (1988) pp. 14–16 (in English and Russian).

Textbook of Anesthesiology. Moscow, the Meditsina Publishers (1994) pp. 10–13 (in English and Russian).

"Side Effects of Drugs." The Meditsina Publishers, Moscow (1983) pp. 1–6 (in English and Russian).

Usoltseva S.V., et al., "1,3,4–Thiadiazines: Method of Synthesis and Reactivity." Khim. Geterotsikl. Soedin No. 4 (1991) pp. 435–448 And English comments thereon.

Novikova A.P., et al. "Synthesis and Properties of Functional Derivatives of 1,3,4. Thiadiazines . . . " Khim. Geterotsikl. Soedin No: 11 (1991) pp. 1443–1457 And English comments thereon.

Rasina L.N., et al. "On Some Mechanisms of Action of Radioprotectors of Various Chemical Classes In Intestinal Syndrome" Radiobiologiya, 30(2) (1990) pp. 162–165 And English comments thereon.

Belik A.V. et al., "Prediction of A Class of Strong Toxicity of 1,3,4–Thiadiazine Derivatives" Khim–Farm. Zh., 26(3), (1992) pp. 62–64 And English comments thereon.

Perova N.M. et al., "Transformation of 2–Cycloalkylimino–6H–1–3–4–Thiadiazines under UV Irradiation" Khim. Geterotsikl. Soedin., No. 4, (1993) pp. 565–600 And English comments thereon.

Patent Abstracts of Japan of JP 06253976 Dated Sep. 13, 1994.

Primary Examiner—John M. Ford
Attorney, Agent, or Firm—Ladas & Parry

[57] ABSTRACT

Substituted 6-R-1,3,4-thiadiazin-2-amines of the following general formula:

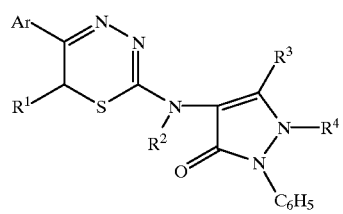

wherein Ar is phenyl or phenyl optionally substituted with one or more chloro, bromo atoms, $C_1$–$C_4$ alkoxy or $C_1$–$C_4$ alkyl groups; $R^1$ and $R^2$ are each independently hydrogen atom or $C_1$–$C_4$ alkyl moiety; and $R^3$ and $R^4$ are independently selected from $C_1$–$C_4$ alkyl groups and pharmaceutically acceptable salts thereof, the use of them as anaesthetics, cardiovascular and hypometabolic agents and pharmaceutical compositions containing them.

40 Claims, No Drawings

SUBSTITUTED 6-R-1,3,4-THIADIAZINE-2-AMINES, THE USE THEREOF AS ANAESTHETIZING, CARDIOVASCULAR AND HYPOMETABOLIC AGENTS, AND A PHARMACEUTICAL COMPOSITION CONTAINING THEM

This is a 371 of PCT/RU95/00285 filed Dec. 28, 1995.

TECHNICAL FIELD

This invention relates to novel 6-R-1,3,4-thiadiazin-2-amine derivatives, to the use of them in medicine and veterinary as anaesthetics, cardiovascular and hypometabolic agents and to pharmaceutical compositions containing them.

BACKGROUND OF THE INVENTION

Anaesthesia may generally be described as a state in which noxious events such as surgical procedures are rendered imperceptible by the body, the state being accompanied either by loss of consciousness (general anaesthesia) or no loss of consciousness (local anaesthesia). A complete or general anaesthetic given by inhalation or intravenous route produces a state of profound sleep and loss of motor activity (hypnosis), analgesia, muscle relaxation and protection against the increase in blood pressure and heart rate resulting from surgical stress. Anaesthetics generally display hypometabolic activity and frequently act as respiratory or cardiovascular depressants. Certain anaesthetics may be used to produce deliberate hypotensive effects which are very valuable in intracranial and other surgical procedures. Although a large number of agents having anaesthetic and cardiovascular activity have been identified and/or commercialised, there is a continuing need for now materials having hypometabolic activity, which are valuable for inducing sleep, reduction in motor activity, hypotension, bradycardiac, hypocoagulative, anti-aggregant and other hypobiosis effects such as reduced oxygen consumption and reduced body temperature, which would be valuable for use in complex surgical procedures or in the treatment of life threatening and/or traumatic situations such as brain stroke and myocardial infarction, and which have excellent potency, duration and CNS and cardiovascular toxicity profiles with absence of side effects such as tremor, convulsions and irregular breathing and heart beat.

There is considerable body of data concerning 6-R-1,3,4-thiadiazin-2-amines (for reviews see [1–3]). Also patent literature provides data on myo-relaxant [4–7], sedative [8,9], spasmolytic [10–12] and other types of biological activity [3]. A number of 5-aryl derivatives of 1,3,4-thiadiazines have been specifically described in the art [14–20] as well as 6-alkyl and 6-phenyl analogs thereof [13 and 21]. The value of 6-R-1,3,4-thiadiazin-2-amines as hypometabolic anaesthetics and cardiovascular agents has not hitherto been recognised however. Moreover, many of the5e compounds are apparently novel and have not been previously described in the literature.

The prior art on 6-R-1,3,4-thiadiazin-2-amines includes:
1. H. Beyer, Z. Chem., Bd.9, S. 361, (1969).
2. S. V. Usoltseva, G. P. Andronnikova, and V. S. Mokrushin, khim. Geterotsikl. Soedin., No 4, 435, (1991).
3. A. P. Novikova, N. M. Perova, and O. N. Chupaichin, Khim. Goereotsikl. Soedin., No 11, 1443, (1991).
4. W. D. Jones and F. P. Miller. US-A-4,309,426 (1982).
5. W. D. Jones and F. P Miller. BE-A-884,991 (1980).
6. W. D. Jones and F. P. Miller. DE-A-3,042,295 (1982).
7. FR-A-2,493,844 (1982).
8. US-A-4,272,532 (1982).
9. F. P. Miller and W. D. Jones. BE-A-884,990 (1980).
10. W. D. Jones and F. P. Miller. DE-A-3,031,703 (1981).
11. Fisons PLC, Japan Kokai, Toroyo Koho JP-A-6253976.
12. W. D. Pfeiffer and E. Bulka, DD-A-220311 (1985).
13. N. Yoshida, K. Tranaka, and Y. Iizuk. Japan Kokai 7438839 (1974).
14. L. N. Pasina, O.N. Chupakhin and M. V. Chibiryak. Radiobiologiya, 30(2), 162–165 (1990).
15. A. V. Belik et al, Khjim.-Farmi. Zh., 26(3), 62–64 (1992).
16. N. M. Perova et al, Kchim. Geterotsikl. Soedin., No 4, 565–566 (1993).
17. E Bulka and W. D. Pfeiffer. DD-A-289824.
18. W. D. Pfeiffer and E Bulka, Synthesis, No 7, 485–486 (1977).
19. T Werner et al, US-A-4,940,790 (1990).
20. A. P. Novikova et al1, SU-A-1726478.
21. E Bulka et al, DD-A-228248.

SUMMARY OF THE INVENTION

According to one aspect off the invention, there is provxided the use off the substituted 6-R,-1,3,4-thiadiazin-2-amines of the following general formula as anaesthetic or cardiovascular agents:

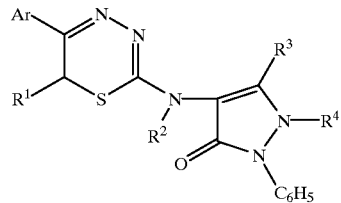

wherein Ar is phenyl or phenyl substituted with one or more atoms of chloro, bromo, $C_1$–$C_4$ alkcoxy or $C_1$–$C_4$ alkyl groups; $R^1$ and $R^2$ are each independently hydrogen atom or $C_1$–$C_4$ alkyl moiety; and $R^3$ and $R^4$ are each independently selected from $C_1$–$C_4$ alkyl groups; and pharmaceutically acceptable salts thereof.

According to a further aspect of the invention, there is provided novel substituted 6-R-1,3,4-thiadiazin- 2-amines of the general formula set out above.

According to a still further .aspect of the invention, there is provided pharmaceutical compositions comprising one or more substituted 6-R-1,3,4-thiadiazin- 2-amines as an active compound or pharmaceutically acceptable salts thereof.

DISCLOSURE OF THE INVENTION 1,3,4-Thiadiazines suitable for use herein contain at the 5 position of the thiadiazine ring unsubstituted phenyl or phenyl substituted with one or more straight or branched chain $C_1$–$C_4$ alkyl, alkenyl, alkoxy or acyloxy groups, one or more hydroxy groups or halogen atoms. In preferred compounds of this formula Ar represents unsubstituted phenol or phenyl Substituted with one or more alkyl, alkoxy groups, chloro or bromo atoms, substitution preferably being at 3- or 4-positions of the aryl moiety., In addition compounds contain at the 2 position of the thiadiazine ring the residue of 4-amino- 1-phenyl-2,3-dialkylpyrazol-5-one or 4-(N-alkylamino)-1-phenyl-2,3-dialkylpyrazol-5-one in which the phenyl moiety is unsubstituted phenyl or phenyl substituted with $C_1$–$C_4$ alkyl, alkenyl, alkoxy or acyloxy groups, one or more hydroxy groups or halogen atoms.

Moreover compounds may be substituted at the 6 position of the thiadiazine ring ($P^1$) and/or at the 2-amino position of the thiadiazine ring ($R^2$) with a one of $C_1$–$C_4$ alkyl group.

According to the invention the 1,3,4-thiadiazines described above may be prepared by the reaction of an α-haloarylalkanone having the formula Ar—CO—CH($R^1$)X with a thiosemicarbazide of formula $NH_2$—NH—CS—$NR^2$Y, wherein Ar, $R^1$ and $R^2$ are as defined above, X is halo, preferably chloro or bromo atom, and Y is 1-phenyl-2,3-dialkylpyrazol-5-one-4-yl in which the alkyl or dialkyl groups are preferably straight or branched chain $C_1$-$C_4$ alkyl and in which the phenyl moiety is unsubstituted phenyl or phenyl substituted with $C_1$–$C_4$ alkyl, alkenyl, alkoxy or acyloxy groups, or one or more halogen atoms or hydroxy-groups.

The 1,3,4-thiadiazines may be isolated and/or used herein in free form or they may be transformed into additive salts with pharmacological acceptable mineral or organic acids. Suitable for the preparation of acid addition salts are, for example, mineral acids, such as hydrobromic acid, hydrochloric acid, sulfuric acid or phosphoric acid; organic carboxylic acids, such as acetic acid, lactic acid, maleic acid, fumaric acid, oxalic acid, tartalic acid, citric acid or gluconic acid; or organic sulfonic acids, such as benzenesulfonic acid, p-.

The α-haloarylalkanones used as starting materials in the manufacture of the thiadiazines described herein are known from the literature or may be prepared from aylatanones by reacting with a suitable halogenating agent according to the methods described in Houben-Weyl, Vol.4 (1960), pp.171–189. Suitable compounds include, for example, α-bromo-1-arylethanone and α-bromo-2-arylbutanone in which aryl is selected from phenyl or substituted phenyl and which are prepared by halogenating the correspondent substituted 1-arylalkanones using bromine or copper(II) bromide according to the method or King and Ostrum, J. Org. Chem. 29 (1964), pp.3459–61.

The substituted thiosemicarbazides used as starting materials are mostly known from the literature or may be prepared by the methods described in Houben-Weyl, Vol. E 4, pp. 506–15, and by K. Jensen et al., Acta Chem. Scand. 22 (1968), pp. 1–50. Thus, the thiosemicarbazide may be obtained by adding hydrazine to isothiocyanates or by reacting the appropriate N,N-di-substituted thiocarbamoyl chlorides with hydrazine or by reacting ethyl dithiocarbamates of formula

with hydrazine.

In order to avoid interfering side reactions, these reactions are advantageously carried out in aprotic solvents, such as, for example, chloroform, tetrachloromethane, diethyl ether or dioxan.

The reaction of α-haloarylalkanones with thiosemicarbazide is expediently carried out using equimolar amounts of the two reactants in a solvent or in a diluent which is inert towards the reactants. Suitable for this purpose are, in particular, lower alcohol, such as methanol, ethanol, n-propanol, isopropanol and the various butanols, or ethylacetate, and mixtures thereof, however ethanol is preferable. The reaction is generally carried out at the temperature in the range about 20° C. to the reflux temperature of the reaction mixture, preferably about 20° C. to 70° C. Depending on the reactivities of the reagents, the type of the reaction medium and the reaction temperature, the time which is needed to conduct the reaction may be varied in the range from about 5 minutes to 2 hours. The final products are usually recrystallized in analytically pure form on slow cooling of the reaction mixture.

Depending on their solubility the compounds may be administered either by the oral route or via a parenteral injection in a solution form. They may be administered alone, for example in the form of microcapsules, as well as the mixture with one another or in a combination with suitable adjuvants and/or excipients.

Thus the present invention further relates to the pharmaceutical compositions comprising an effective amount of at least one of the thiadiazine compounds as defined above, or at least one of its acid addition salts, in combination with pharmaceutically suitable and physiologically acceptable excipients, diluents and/or other adjuvants suitable solid or liquid galenic formulations include, for example, granules, powders, coated tablets, tablets, (micro)capsules, suppositories, syrups, elixirs, suspensions, emulsions, drops or injectable solutions, as well as preparations having a protracted release of active compound, in the production of which adjuvants, such as excipients, disintegrants, binders, coating agents, swelling agents, glidants, usually used. Suitable adjuvants include, for example, magnesium carbonate, titanium dioxide, lactose, mannitol and other sugars, talc, lactalbumin, gelatine, starch, cellulose and derivatives thereof, animal and vegetable oils, polyethylene glycol5, and solvents such as sterile water and monohydric or polyhydric alcohols, for example glycerol.

The pharmaceutical preparations are preferably manufactured and administered in dosage units, each unit contains as active component a certain dose of at least one thiadiazine compound and/or at least one corresponding acid addition salt. In the case of injectable solutions the thiadiazine is preferably administered in dosages in the range from about 10 to about 600, preferably from about 20 to about 500, more preferably from about 30 to about 400 mg/kg.

Compounds suitable for use herein are represented by the following examples:

1. 2-N-Methyl-N-(1-phenyl-2,3-dimethylpyrazol-5-one-4-yl)-amino-5-phenyl-6H-l,3,4-thiadiazine;
2. 2-N-Methyl-N-(1-phenyl-2,3-dimethylpyrazol-5-one-4-yl)-amino-5-(4-bromophenyl)-6H-1,3,4-thiadiazine;
3. 2-N-(1-Phenyl-2,3-dimethylpyrazol-5-one-4-yl)-amino-5-phenyl-6H-1,3,4-thiadiazine:
4. 2-N-Methyl-N-(1-phenyl-2, 3-dimethylpyrazol-5-one-4-yl)-amino-5-phenyl-6H-6-ethyl-1, 3,4-thiadiazine;
5. 2-N-(1-Phenyl-2,3-dimethylpyrazol-5-one-4-yl)-amino-5-phenyl-6H-6-ethyl-1,3,4-thiadiazine;
6. 2-N-Methyl-N-(1-phenyl-2,3-dimethylpyrazol-5-one-4-yl)-amino-5-(4-ethoxyphenyl)-6H-1,3,4-thiadiazine;
7. 2-N-Methyl-N-(1-phenyl-2,3-dimethylpyrazol-5-one-4-yl)-amino-5-(4-chlorophenyl)-6K-l,3,4-thiadiazine;
8. 2-N-(1-Phenyl-2,3-dimethylpyrazol-5-one-4-yl)-amino-5-(3-bromophenyl)-6H-1,3,4-thiadiazine;
9. 2-N-Methyl-N-(1-phenyl-2,3-dimethylpyrazol-5-one-4-yl)-amino-5-(3-bromophenyl)-6H-1,3,4-thiadiazine.

EXAMPLES

All compounds were obtained in 60–80% yields by condensation of a-haloketones with the corresponding 4-substituted thiosemicarbazides, proceeding smoothly on heating in ethanol. Evidence for the structure of the compounds is provided by their spectral data (UV, IR, $^1$H NMR);

their purity is confirmed by thin-layer chromatography and elemental analysis.

Example 1

2-N-Methyl-N-(1-phenyl-2,3-dimethylpyrazol-5-one-4-yl)-amino-5-phenyl-6H-1,3,4-thiadiazine.

The compound 1 was prepared by heating of 2 g (0.01 mole) of α-bromoacetophenone with 2.9 g (0.01 mole) 4-methyl-4-(1-phenyl-2,3-dimethylpyrazol-5-one-4-yl)-thiosemicarbazide in ethanol for 20 minutes. The reaction mixture was cooled and made alkaline with a diluted solution of ammonia3 to adjust pH 8–9. A colourless precipitate formed was filtered off, recrystallized from 30% water-ethanol, and dried. Yield 2.7 g (70%). M.p. 154–156° C. $R_f$=0.6 (eluent: ethanol-chloroform 1:8). Found, %: C 64.4; H 5.4; N 17.7. $C_{21}H_{21}N_5OS$. Calculated, %: C 64.4; H 5.4; N 17.9. $^1H$ NMR, DMSO-$d_6$, δ, ppm: 2.2 (3H, s, $CH_3$) 3.2 (3H, br. s, $NCH_3$); 3.35 (3H, br. s, $NCH_3$); 3.7 (2H, s, $CH_2S$); 7.4–7.9 (10H, m, two $C_6H_5$).

Example 2

2-N-Methyl-N-(1-phenyl-2,3-dimethylpyrazol-5-one-4-yl)-amino-5-(4-bromophenyl)-6H-1,3,4-thiadiazine.

The compound 2 is obtained in the same manner as in Example 1 starting from α-bromo-4-bromo-acetophonone and 4-methyl-4-(1-phonyl-2,3-dimethylpyra-zol-5-one-4-yl)thiosemicarbazide. Yield 72%. M.p. 169–170° C. $R_f$=0.5 (eluent: ethanol-chloroform 10:1). Found, %: C 53.6; H 4.3; N 14.6. $C_{21}H_{20}BrN_5OS$. Calculated, %: C 53.6; H 4.3; N 14.9. $^1H$ NMR, DMSO-$d_6$, δ, ppm: 2.2 (3H, s, $CH_3$), 3.2 (3H, br. s, $NCH_3$);3.35 (3H, br. s, $NCH_3$); 3.65(2H, s, $CH_2S$); 7.4–8.0 (9H, m, $C_6H_5$ and $C_6H_4$).

Example 3

2-N-(1-Phenyl-2,3-dimethylpyrazol-5-one-4-yl)-amino-5-phenyl-6H-1,3,4-thiadiazine.

The compound 3 is obtained in the same manner as in Example 1 starting from α-bromoacetophenone and 4-(1-phenyl-2,3-dimethylpyrazol-5-one-4-yl)-thiosemicarbazide. Yield 88%. M.p. 112–114° C. $R_f$=0.58 (eluent: ethanolchloroform 1:8). Found, %: C 63.5; H 5.2; N 18.4. $C_{20}H_{19}N_5OS$. Calculated, %: C 63.6; H 5.1; N 18.5. $^1H$ NMR, DMSO-$d_6$, δ, ppm: 2.2 (3H, s, $CH_3$); 3.1 (3H, s, $NCH_3$); 3.9 (2H, s, $CH_2S$); 7.3–8.0 (10H, m, two $C_6H_5$).

Example 4

2-N-Methyl-N-(1-phenyl-2,3-dimethylpyrazol-5-one-4-yl)-amino-5-phonyl-6H-6-ethyl-1,3,4-thiadiazine.

The compound 4 was prepared by heating of 0.5 g (0:002 mole) of α-bromobutyrophenone with 0.5 g (0. 002 mole) 4-methyl-4-(1-phenyl-2,3-dimethylpyrazol-5-one-4-yl)-thiosemicarbazide in 10 ml of ethanol for 20 minutes. The mixture was cooled, made alkaline with a 7% solution of ammonia up to pH 9, and hold for 30 minutes. A yellowish residue was filtered off, crystallised from a mixture of water and isopropanol 30:70, and dried. Yield 0.6 g(75%). M.p. 86–89° C. $R_f$=0.35 (eluent: ethanol-chloroform 1:10). Found, %: C 64.4; H 6.0; N 16.7. $C_{23}H_{25}N_5OS$. Calculated, %: C 64.5; H 6.2; N 16.3. $^1H$ NMR in DMSO-$d_6$, δ, ppm: 0.9 (3H, t, —$CH_3$); 2.2 (3H, s, $CH_3$): 3.05 (2H, q, —$CH_2$—); 3.18 (3H, br. s, $NCH_3$); 3.30 (3H, br. s, $NCH_3$); 4.25 (1H, m, =CHS); 7.2–8.1(10H, m, two $C_6H_5$).

Example 5

2-N-(1-Phenyl-2,3-dimethylpyrazol-5-one-4-yl)-amino-5-phenyl-6H-6-ethyl-1,3,4-thiadiazine.

The compound 5 is obtained in the same manner as in Examples 1–4 starting from a-bromobutyrophenone and 4-(1-phenyl-2,3-dimethylpyrazol-5-one-4-yl)-thiosemicarbazide. Yield 74%. M.p. 79–80° C. $R_f$=0.32 teluent: ethanol-chloroform 1:10). Found, %: C 63.3; H 5.7; N 17.6. $C_{22}H_{23}N_5OS·0.5H_2O$. Calculated, %: C 63.8; H 5.8: N 17.8. $^1H$ NMR in DMSO-$d_6$, δ, ppm; 1.05 (3H, t, —$CH_3$); 1.70 (2H, m, $CH_2$); 2.20 (3H, s, $CH_3$); 3.10 (3H, br. s, $NCH_3$); 4.35 (1H, m, =CHS); 7.0–8.1(10H, m, two $C_6H_5$).

Example 6

2-N-Methyl-N-(1-phenyl-2,3-dimethylpyrazol-5-one-4-yl)-amino-5-(4-ethoxyphenyl)-6H-1,3,4-thiadiazine.

The compound 6 was prepared by heating 2.4 g (0.01 mole) of 4-ethoxy-α-bromoacetophenone with 2.8 g (0.01 mole) 4-methyl-4-(1-phenyl-2,3-dimethylpyrazol-5-one-4-yl)-thiosemicarbazide in 100 ml of absolute ethanol for 20 minutes. The mixture was cooled, made alkaline with a 7% solution of ammonia up to pH 8–9. A yellowish residue was filtered off, crystallised from a mixture of water and ethanol 80:20, and dried. Yield 3.5 g (74%). M.p. 164–165° C. $R_f$=0.25 (eluent: ethanol-chloroform 1:10). Found, %: C 63.3; H 5.9; N 15.8. $C_{23}H_{25}N_5O_2S$. Calculated, %. C 63.4; H 5.8; N 16.1. $^1H$ NMR in DMSO-$d_6$, δ, ppm: 1.34 (3H, t, —$CH_3$); 2.2 (3H, s, $CH_3$); 3.14 (3H, s, $NCH_3$); 3.30 (3H, br.s, $NCH_3$); 3.60 (2H, br. s, $CH_2S$); 4.13 (2H, q, $OCH_2$—); 7.45 (5H, m, $C_6H_5$).

Example 7

2-N-Methyl-N-(1-phenyl-2,3-dimethylpyrazol-5-one-4-yl)-amino-5-(4-chlorophenyl)-6H-1,3,4-thiadiazine.

The compound 7 is obtained in the same manner as in Example 6 starting from 4-chloro-α-bromoacetophenone and 4-methyl-4-(1-phenyl-2,3-dimethylpyrazol-5-one-4-yl)-thiosemicarbazide. Yield 77%. m.p. 178–179° C. $R_f$=0.3 (eluent: ethanol-chloroform 1:10). Found, %; C 57.7; H 4.7; N 15.8. $C_{21}H_{20}ClN_5OS·0.5H_2O$. Calculated, %: C 58.0; H 4.8; N 16.2. $^1H$ NMR in DMSO-$d_6$, δ, ppm: 2.20 (3H, s, $CH_3$); 3.15 (3H, br. s, $NCH_3$); 3.30 (3H, br. s, $NCH_3$); 3.65 (2H, s, $CH_2S$); 7.3–8.0 (9H, m, $C_6H_5$ and $C_6H_4$).

Example 8

2-N-(1-Phenyl-2,3-dimethylpyrazol-5-one-4-yl)-amino-5-(3-bromophenyl)-6H-1,3,4-thiadiazine.

The compound 8 is obtained in the same manner as in Example 6 starting from 3-bromo-α-bromoacetophenone and 4-(1-phenyl-2,3-dimethylpyrazol-5-one-4-yl)-thiosemicarbazide. Yield 76%. M.p. 69–70° C. $R_f$=0.38 (eluent: ethanol-chloroform 1:10). Found, %: C 50.6; H 4.2; N 14.6. $C_{20}H_{18}BrN_5OS·H_2O$. Calculated, %: C 50.2; H 3.9; N 14.8. $^1H$ NMR, DMSO-$d_6$, δ, ppm: 2.20 (3H, s, $CH_3$); 3.10 (3H, br. s, $NCH_3$); 3.95 (2H, s, $CH_2S$); 7.1–8.0 (9H, m, $C_6H_5$ and $C_6H_4$).

Example 9

2-N-Methyl-(1-phenyl-2,3-dimethylpyrazol-5-one-4-yl)-amino-5-(3-bromophenyl)-6H-1,3,4-thiadiazine.

The compound 9 is obtained in the same manner as in Example 6 starting from 3-bromo-α-bromo-acetophenone and 4-N-methyl-(1-phenyl-2,3-dimethylpyrazol-5-one-4-yl) thiosemicarbazide. Yield 82%. M.p. 88–90° C. $R_f$=0.48 (eluent: ethanol-chloroform 1:10). Found, %: C 49.4; H 4.4; N 14.7. $C_{21}H_{20}BrN_5OS·2H_2O$. Calculated. %: C 49.6; H 4.7; N 14.9. $^1H$ NMR, DMSO-$d_6$, δ, ppm: 2.20 (3H, s, $CH_3$); 3.15 (3H, br. s, $NCH_3$); 3.25 (3H, br. s, $NCH_3$); 3.55 (2H, s, $CH_2S$); 7.0–8.2 (9H, m, $C_6H_5$ and $C_6H_4$).

EXPERIMENTAL BIOLOGICAL PART

The hypometabolic activity of the compounds utilised herein was demonstrated as follows. In all cases tests were carried out on mice of the BALB line of 3–4 month age. Non-toxic doses of compounds under test, varying from 60 to 400 mg/kg, were used in all experiments. In the case of water-soluble compounds, agueous solutions of the test compounds were injected intraperitoneally (i.p.), while water-insoluble compounds were introduced orally (p.o.).

In order to demonstrate the effect of the compounds herein on body temperature and oxygen consumption, in vivo experiments were run using 5–6 mice per dosage.

Rectal temperature changes (absolute magnitudes in ° C.) were measured using a medicinal electrothermometer TREM-1 (Table 1). The rate of oxygen consumption was monitored by measuring concentration of oxygen in a closed testing unit with optic-acoustic gas analyser MN 5130. The data on oxygen consumption are given in percents relative to the starting content of oxygen taken as 100% (Table 2).

When used in non-toxic doses, all compounds were found to decrease rectal temperature in the range from 3 to 15° C., depending on the structure, dosage and method of introduction. It has been established that some of the tested compounds show sharp drop in body temperature (7–8° C. per 30 minutes), while others demonstrate only moderate effect (7–10° C. per 3 hours), as illustrated in Table 1.

Compound 1 was injected orally in the dose of 0.16 mg/kg (½ $LD_{16}$) and then rectal temperature was measured. After 1 hour the body temperature was 5° C. lower relative to the initial one. During the next 4 hours it decreased further to reach 26.4° C. (which makes a total reduction of 12.5° C.), while in 24 hours the temperature value recovered to the level of 96% of the starting point. The moving activities of the mice were also completely restored. In case of smaller doses (¼ $LD_{16}$ or ⅛ $LD_{16}$), a smaller drop in temperature resulted.

When injected in a dose of ½ $LD_{16}$ Compound 1 also caused a remarkable drop in oxygen consumption: 76% of the starting level after 5 minutes with maximum decrease of 50% after 60–90 minutes (Table 2). The period of maximum decreasing of temperature is accompanied by profound akinesia and suppression of reflectory function, however no tremor or convulsion syndromes were observed.

TABLE 1

Effects of 1,3,4-thiadiazines on body temperature (° C.) in experiments on mice

| Compound | Dose,mg/kg (mM/kg) | Administration | Time of measurements in minutes | | | |
|---|---|---|---|---|---|---|
| | | | 0 | 30 | 60 | 90 |
| 1 | 63.0(0.16) | p.o. | 38.9 | 36.7 | 30.9 | 30.9 |
| 6 | 69.6(0.15) | p.o. | 38.7 | 32.0 | 32.3 | 32.3 |
| | | | 120 | 180 | 240 | 300 |
| 1 | 63.0(0.16) | p.o. | 29.1 | 27.3 | 26.5 | 26.4 |
| 6 | 69.6(0.15) | p.o. | 32.3 | 32.9 | 33.3 | 33.7 |

TABLE 2

Effect of Compound 1 on body temperature (T) and consumption of oxygen ($O_2$) in experiments on mice

| Compound | dose (1/2$LD_{16}$) mg/kg (mM/kg) | Index | Time in measurements in minutes | | | | | | | | | |
|---|---|---|---|---|---|---|---|---|---|---|---|---|
| | | | 0 | 5 | 15 | 30 | 60 | 90 | 120 | 180 | 240 | 300 |
| 1 | 58.0(0.15) | T. ° C. | 38.9 ± 0.2 | 38.1 ± 0.1 | 37.5 ± 0.3 | 36.7 ± 0.3 | 33.8 ± 0.8 | 30.9 ± 0.8 | 29.1 ± 0.7 | 27.3 ± 0.5 | 26.5 ± 0.5 | 26.4 ± 0.6 |
| | | $O_2$, % | 100 | — | 76.4 | 63.2 | 57.8 | 57.7 | 60.5 | 80 | 77.1 | 78.9 |

What is claimed is:

1. A 6-R-1,3,4-thiadiazin-2-amine of the formula

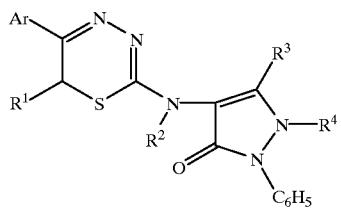

wherein Ar is phenyl or phenyl optionally substituted with one or more chloro, bromo atoms, $C_1$–$C_4$ alkoxy or $C_1$–$C_4$ alkyl groups; $R^1$ and $R^2$ are each independently hydrogen atom or $C_1$–$C_4$ alkyl moiety; and $R^3$ and $R^4$ are independently selected from $C_1$–$C_4$ alkyl groups; and pharmaceutically acceptable salts thereof.

2. A 6-R-1,3,4-thiadiazin-2-amine according to claim 1 which is 2-N-methyl-N-(1-phenyl-2,3-dimethyl-pyrazol-5-one-4-yl)-amino-5-phenyl-6H-1,3,4-thiadiazine or a pharmaceutically acceptable salt thereof.

3. A method of inducing anaesthesia which comprises administering an anaesthetically effective amount of 6-R-1,3,4-thiadiazin-2-amines as defined in claim 1 of the formula:

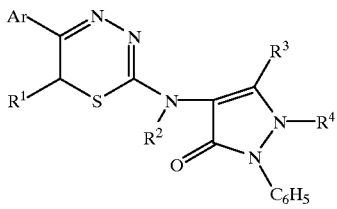

wherein Ar is phenyl or phenyl optionally substituted with one or more chloro, bromo atoms, $C_1$–$C_4$ alkoxy or $C_1$–$C_4$ alkyl groups; $R^1$ and $R^2$ are each independently hydrogen atom or $C_1$–$C_4$ alkyl moiety; and $R^3$ and $R^4$ are independently selected from $C_1$–$C_4$ alkyl groups and pharmaceutically acceptable salts thereof to a patient.

4. A method according to claim 3 wherein the 6-R-1,3,4-thiadiazin-2-amine is 2-N-methyl-N-(1-phenyl-2,3-dimethyl-pyrazol-5-one-4-yl)-amino-5-phenyl-6H-1,3,4-thiadiazine.

5. A pharmaceutical composition comprising an effective amount of an active ingredient and pharmaceutically suitable excipient, diluent and/or other adjuvants, characterized in that said composition comprises as an active ingredient one or more compounds of the formula:

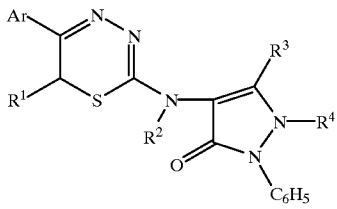

wherein Ar is phenyl or phenyl optionally substituted with one or more chloro, bromo atoms, $C_1$–$C_4$ alkoxy or $C_1$–$C_4$ alkyl groups; $R^1$ and $R^2$ are each independently hydrogen atom or $C_1$–$C_4$ alkyl moiety; and $R^3$ and $R^4$ are independently selected from $C_1$–$C_4$ alkyl groups and pharmaceutically acceptable salts thereof.

6. The pharmaceutical composition according to claim 5 characterized in that it comprises as an active compound the 6-R-1,3,4-thiadiazin-2-amine as defined in claim 1 which is 2-N-methyl-N-(1-phenyl-2,3-dimethylpyrazol-5-one-4-yl)-amino-5-phenyl-6H-1,3,4-thiadiazine or a pharmaceutically acceptable salt thereof.

7. A 6-R-1,3,4-thiadiazin-2-amine according to claim 1, which is 2-N-methyl-N-(1-phenyl-2,3-dimethylpyrazol-5-one-4-yl)-amino-(4-bormophenyl)-6H-1,3,4-thiadiazine.

8. A 6-R-1,3,4-thiadiazin-2-amine according to claim 1, which is 2-N-(1-phenyl-2,3-di-methylpyrazol-5-one-4-yl)-amino-5-phenyl-6H-1,3,4-thiadiazine.

9. A 6-R-1,3,4-thiadiazin-2-amine according to claim 1, which is 2-N-methyl-N-(1-phenyl-2,3-dimethylpyrazol-5-one-4-yl)-amino-5-phenyl-6H-6-ethyl-1,3,4-thiadiazine.

10. A 6-R-1,3,4-thiadiazin-2-amine according to claim 1, which is 2-N-(1-phenyl-2,3-dimethylpyrazol-5-one-4-yl)-amino-5-phenyl-6H-6-ethyl-1,3,4-thiadiazine.

11. A 6-R-1,3,4-thiadiazin-2-amine according to claim 1, which is 2-N-methyl-N-(1-phenyl-2,3-dimethylpyrazol-5-one-4-yl)-amino-5-(4-ethoxyphenyl)-6H-1,3,4-thiadiazine.

12. A 6-R-1,3,4-thiadiazin-2-amine according to claim 1, which is 2-N-methyl-N-(1-phenyl-2,3-dimethylpyrazol-5-one-4-yl)-amino-5-(4-chlorophenyl)-6H-1,3,4-thiadiazine.

13. A 6-R-1,3,4-thiadiazin-2-amine according to claim 1, which is 2-N-(1-phenyl-2,3-dimethylpyrazol-5-one-4-yl)-amino-5-(3-bromophenyl)-6H-1,3,4-thiadiazine.

14. A 6-R-1,3,4-thiadiazin-2-amine according to claim 1, which is 2-N-methyl-N-(1-phenyl-2,3-dimethylpyrazol-5-one-4-yl)-amino-5-(3-bormophenyl)-6H-1,3,4-thiadiazine.

15. A method according to claim 3, wherein the 6-R-1,3,4-thiadiazin-2-amine is 2-N-methyl-(1-phenyl-2,3-dimethylpyrazol-5-one-4-yl)-amino-5-(4-bromophenyl)-6H-1,3,4-thiadiazine.

16. A method according to claim 3, wherein the 6-R-1,3,4-thiadiazin-2-amine is 2-N-(1-phenyl-2,3-dimethylpyrazol-5-one-4-yl)-amino-5-phenyl-6H-1,3,4-thiadiazine.

17. A method according to claim 3, wherein the 6-R-1,3,4-thiadiazin-2-amine is 2-N-methyl-N-(1-phenyl-2,3-dimethylpyrazol-5-one-4-yl)-amino-5-phenyl-6H-6-ethyl-1,3,4-thiadiazine.

18. A method according to claim 3, wherein the 6-R-1,3,4-thiadiazin-2-amine is 2-N-(1-phenyl-2,3-dimethylpyrazol-5-one-4-yl)-amino-5-phenyl-6H-6-ethyl-1,3,4-thiadiazine.

19. A method according to claim 3, wherein the 6-R-1,3,4-thiadiazin-2-amine is 2-N-methyl-N-(1-phenyl-2,3-dimethylpyrazol-5-one-4-yl)-amino-5-(4-ethoxyphenyl)-6H-1,3,4-thiadiazine.

20. A method according to claim 3, wherein the 6-R-1,3,4-thiadiazin-2-amine is 2-N-methyl-N-(1-phenyl-2,3-dimethylpyrazol-5-one-4-yl)-amino-5-(4-chlorophenyl)-6H-1,3,4-thiadiazine.

21. A method according to claim 3, wherein the 6-R-1,3,4-thiadiazin-2-amine is 2-N-(1-phenyl-2,3-dimethylpyrazol-5-one-4-yl)-amino-5-(3-bromophenyl)-6H-1,3,4-thiadiazine.

22. A method according to claim 3, wherein the 6-R-1,3,4-thiadiazin-2-amine is 2-N-methyl-N-(1-phenyl-2,3-dimethylpyrazol-5-one-4-yl)-amino-5-(3-bormophenyl)-6H-1,3,4-thiadiazine.

23. A method for treating cardiovascular or hypometabolic disease which comprises administering to a patient in need of such treatment a therapeutically effective amount of a 6-R-1,3,4-thiadiazin-2-amine as defined in claim 1.

24. A method according to claim 23, wherein said 6-R-1,3,4-thiadiazin-2-amine is 2-N-methyl-N-(1-phenyl-2,3-dimethylpyrazol-5-one-4-yl)-amino-5-phenyl-6H-1,3,4-thiadiazine.

25. A method according to claim 23, wherein said 6-R-1,3,4-thiadiazin-2-amine is 2-N-methyl-N-(1-phenyl-2,3,dimethylpyrazol-5-one-4-yl)-amino-5-(bromophenyl)-6H-1,3,4-thiadiazine.

26. A method according to claim 23, wherein said 6-R-1,3,4-thiadiazin-2-amine is 2-N-(1-phenyl-2,3-di-methylpyrazol-5-one-4-yl)-amino-5-phenyl-6H-1,3,4-thiadiazine.

27. A method according to claim 23, wherein said 6-R-1,3,4-thiadiazin-2-amine is 2-N-methyl-N-(1-phenyl-2,3-dimethylpyrazol-5-one-4-yl)-amino-5-phenyl-6H-6-ethyl-1,3,4-thiadiazine.

28. A method according to claim 23, wherein said 6-R-1,3,4-thiadiazin-2-amine is 2-N-(1-phenyl-2,3-dimethylpyrazol-5-one-4-yl)-amino-5-phenyl-6H-6-ethyl-1,3,4-thiadiazine.

29. A method according to claim 23, wherein said 6-R-1,3,4-thiadiazin-2-amine is 2-N-methyl-N-(1-phenyl-2,3-dimethylpyrazol-5-one-4-yl)-amino-5-(4-ethoxyphenyl)-6H-1,3,4-thiadiazine.

30. A method according to claim 23, wherein said 6-R-1,3,4-thiadiazin-2-amine is 2-N-methyl-N-(1-phenyl-2,3-dimethylpyrazol-5-one-4-yl)-amino-5-(4-chlorophenyl)-6H-1,3,4-thiadiazine.

31. A method according to claim 23, wherein said 6-R-1,3,4-thiadiazin-2-amine is 2-N-(1-phenyl-2,3-dimethylpyrazol-5-one-4-yl)-amino-5-(3-bromophenyl)-6H-1,3,4-thiadiazine.

32. A method according to claim 23, wherein said 6-R-1,3,4-thiadiazin-2-amine is 2-N-methyl-N-(1-phenyl-2,3-dimethylpyrazol-5-one-4-yl)-amino-5-(4-bormophenyl)-6H-1,3,4-thiadiazine.

33. A pharmaceutical composition according to claim 5, wherein said compound is 2-N-methyl-N-(1-phenyl-2,3-dimethylpyrazol-5-one-4-yl)-amino-5-(4-bromophenyl)-6H-1,3,4-thiadiazine.

34. A pharmaceutical composition according to claim 5, wherein said compound is 2-N-(1-phenyl-2,3-dimethylpyrazol-5-one-4-yl)-amino-5-phenyl-6H-1,3,4-thiadiazine.

35. A pharmaceutical composition according to claim 5, wherein said compound is 2-N-methyl-N-(1-phenyl-2,3-dimethylpyrazol-5-one-4-yl)-amino-5-phenyl-6H-6-ethyl-1,3,4-thiadiazine.

36. A pharmaceutical composition according to claim 5, wherein said compound is 2-N-(1-phenyl-2,3-dimethylpyrazol-5-one-4-yl)-amino-5-phenyl-6H-6-ethyl-1,3,4-thiadiazine.

37. A pharmaceutical composition according to claim 5, wherein said compound is 2-N-methyl-N-(1-phenyl-2,3-dimethylpyrazol-5-one-4-yl)-amino-5-(4-ethoxyphenyl)-6H-1,3,4-thiadiazine.

38. A pharmaceutical composition according to claim 5, wherein said compound is 2-N-methyl-N-(1-phenyl-2,3-dimethylpyrazol-5-one-4-yl)-amino-5-(4-chlorophenyl)-6H-1,3,4-thiadiazine.

39. A pharmaceutical composition according to claim 5, wherein said compound is 2-N-(1-phenyl-2,3-dimethylpyrazol-5-one-4-yl)-amino-5-(3-bromophenyl)-6H-1,3,4-thiadiazine.

40. A pharmaceutical composition according to claim 5, wherein said compound is 2-N-methyl-N-(1-phenyl-2,3-dimethylpyrazol-5-one-4-yl)-amino-5-(3-bormophenyl)-6H-1,3,4-thiadiazine.

* * * * *